United States Patent
Chatterjee et al.

(10) Patent No.: US 6,471,136 B1
(45) Date of Patent: Oct. 29, 2002

(54) BIOSENSORS FOR MONITORING AIR CONDITIONING AND REFRIGERATION PROCESSES

(75) Inventors: Sharmista Chatterjee, Cincinnati, OH (US); Sunita Satyapal, E. Hampton, CT (US); Harvey Michels, W. Hartford, CT (US); Richard Meinzer, Glastonbury, CT (US); Jared Barney Hertzberg, Manchester, CT (US)

(73) Assignee: Carrier Corporation, Syracuse, NY (US)

( * ) Notice: Subject to any disclaimer, the term of this patent is extended or adjusted under 35 U.S.C. 154(b) by 0 days.

(21) Appl. No.: 09/603,178

(22) Filed: Jun. 26, 2000

Related U.S. Application Data

(60) Provisional application No. 60/141,396, filed on Jun. 29, 1999.

(51) Int. Cl.[7] ............................................. G05D 23/00
(52) U.S. Cl. ................................................... 237/2 B
(58) Field of Search ........................... 237/2 B, 8 A, 237/12; 62/127, 129

(56) References Cited

U.S. PATENT DOCUMENTS

| | | | | |
|---|---|---|---|---|
| 4,789,804 A | * | 12/1988 | Karube et al. | 310/311 |
| 5,056,355 A | * | 10/1991 | Hepher | 73/24.03 |
| 5,457,963 A | | 10/1995 | Cahill-O'Brien et al. | 62/78 |
| 6,008,893 A | * | 12/1999 | Roos et al. | 356/246 |
| 6,192,766 B1 | * | 2/2000 | Gardhagen et al. | 73/863.12 |

FOREIGN PATENT DOCUMENTS

| | | | | |
|---|---|---|---|---|
| DE | 4015506 | | 11/1991 | F24F/3/16 |
| DE | 19536384 | | 4/1997 | G01N/27/12 |
| JP | 2159554 | | 6/1990 | 27/416 |
| JP | 0509328 | | 10/1992 | |
| JP | 05199836 | | 8/1993 | 7/144 |
| WO | 0122730 | | 10/1984 | G01M/3/16 |

* cited by examiner

*Primary Examiner*—Harold Joyce
*Assistant Examiner*—Derek S. Boles
(74) *Attorney, Agent, or Firm*—William W. Habelt

(57) ABSTRACT

A biosensor 10 provides for real time monitoring a selected aspect of an air conditioning or a refrigeration process and system. The biosensor 10 includes a biocomponent element 20 carrying a bioagent 22 operative to detect one or more analytes indicative of the selected aspect of the climate control process to be monitored.

4 Claims, 1 Drawing Sheet

BIOSENSORS FOR MONITORING AIR CONDITIONING AND REFRIGERATION PROCESSES

This application claims the benefit of 60/141,396, filed Jun. 29, 1999

BACKGROUND OF THE INVENTION

The present invention relates in general to biosensors and, more particularly, to biosensors for use in monitoring climate control processes, such as heating, ventilating, air conditioning and refrigeration processes.

Biosensors are chemical sensors comprising three basic elements: a reactive biocomponent element, a base sensor element and an interface element disposed therebetween. The biocomponent includes a bioagent, such as bioactive species or biomimetic species, selected to interact specifically with a particular analyte to be sensed. The bioagent, typically through a biochemical process, acts to bind or convert the analyte into a measurable component. Biocomponents used in conventional sensors include biological species such as enzymes, antigens, antibodies, receptors, tissues, whole cells, cell organelles, bacteria and nucleic acids. The sensor element comprises a physical component operative to generate a measurable output, usually an electrical or optical signal, indicative of the presence of the analyte and, in certain instances, the actual amount of the analyte. Sensor elements used in conventional sensors include, for example, electrochemical devices, optical devices, acoustical devices and calorimetric devices. The interface element comprises a membrane or coating that separates the sensor from the biocomponent and serves as a link between the two. Examples of interfaces used in conventional biosensors include polymer membranes, electropolymerized coatings and self-assembling monomers.

Conventional biosensors include, for example, microcantilever biosensors, bioluminescent bioreporter sensors, fiber optic probe biosensors, porous silicon optical interferrometric biosensors, and biomimetic sensors. Microcantilever biosensors comprise a MEMS sensor chip operatively associated with an electronic readout chip. This type of biosensor has been used for biological sensing using antibody-antigen interaction. Additionally, such microcantilever biosensors have been used to measure concentrations of toluene, acetone, methanol and formaldehyde. The micro-cantilevers typically used in this type of biosensor comprise silicon or silicon nitride.

Bioluminescent bioreporter sensors comprise bioreporter organisms directly interfaced with an integrated circuit. The bioreporter organisms, which may be genetically engineered, luminesce when an analyte is detected and the IC detects the optical signal. Currently, various materials are being considered for entrapment of the cells at or near the light sensing portion of the IC, including agar/agarose, alginate, carrageenan, polyurethane, and ployacrylamide. Entrapment is essential for maintaining population viability, providing nutrients, interfacing with the IC, and providing protection from environmental conditions. Bioluminescent bioreporter integrated circuit sensors have been successfully employed to detect naphthalene, benzene, toluene, ethylbenzene, xylene polychlorinated biphenyl (PCB). Bioluminescent bioreporters have also been designed for detecting isopropylbenzene, monitoring heat shock gene expression, monitoring oxidative stress, detecting of mercury, and detecting alginate production in biofilms.

Fiber optic probe biosensor devices have been developed for remote detection of aerosolized bacteria. One such biosensor device comprises a fiber optic biosensor probe integrated with an automatic fluidics unit, a cyclone type air sampler, a radio receiver and batteries on a small remotely operated airplane. The biosensor is capable of running multiple simultaneous immuno assays in the evanescent wave region of the optical fiber. When the probe is in contact with a sample containing an analyte, an immobilized antibody specifically binds the analyte from the bulk solution. Any fluorophores are also bound in the evanescent region. Excitation of the fluorophore by light in the evanescent region (using a laser fluorimeter) leads to a detectable signal. Fiber optic probes have been used for analyzing clinical samples for pathogens, food samples for toxins, ground water samples for pollutants, and environmental samples for biological warfare agents. One remote biosensor uses a biotin-avidin system to link antibodies on the tapered distal end of the fiber optic probe. This system can easily be adapted for multi analyte sensing by changing the bound antibodies on the fiber optic probe. Use of avidin-biotin cross linking method increases the sensitivity and reduces non specific interactions by passivating the glass surface against non specific antibodies.

Porous silicon based optical interferrometric biosensors change color to signal the presence of various molecules. The basis of this technology is observing the change in the optical interference pattern. Chemical recognition molecules such as strands of DNA or antibodies are seeded on the surface of a porous silicon chip. The effective optical thickness of the medium can be correlated with the order and the wavelength of a peak in the spectral interferrogram. Consequently, the Fourier transform of the intensity-energy relationship can be used to calculate the effective optical thickness of the interference layers. The change of the effective optical thickness (product of refractive index and thickness) caused by the biological binding will shift the interference pattern to longer or shorter wavelength depending on the index-modifying mechanism involved, resulting in the emission of different colors and can be used as a very sensitive method for biosensing. The photoluminiscence of the porous silicon is due to the existence of nano/quantum sized silicon crystals. A portable hand held biosensor has been developed using this technology to detect a wide variety of compounds. This device can be used for detecting DNA, antibodies and biotin/avidin systems.

Biomimetic sensors do not use a biological element per se for detecting an analyte, but rather mimic a biological process using chemical reactions. Biomimetic sensors typically comprise a porous solid state substrate which is transmitive to light, such as, for example, a silica gel, a porous silicon dioxide and a porous, leached borosilicate glass; a light emitting diode and phototransistor for detecting the transmitted light; and a self regenerating chemical sensing agent impregnated into the substrate. In one such biomimetic sensor designed for detection of carbon monoxide, the chemical sensor agent is a supramolecular organometallic chemical complex, which mimics the function of hemoglobin, self assembled onto the surface of the solid substrate. The chemical sensing agents for CO detection are a mixture of soluble palladium salts, molybdenum and/or tungsten salts, copper salts, molecular encapsulants such as alpha cyclodextrin. Upon exposure of the solid state sensor to CO, the chemical reagent undergoes changes in its optical density. In CO free air, the chemical sensing elements can reverse their spectral shift by a self-regeneration process with a rate proportional to the rate of decrease of CO in the environment. The response characteristics (sensitivity and response time) of the sensor can be designed to meet specific standards or applications by controlling the formulation process of the chemical sensing agent. U.S. Pat. 5,063,164, discloses a biomimetic sensor developed for ethylene detection.

SUMMARY OF THE INVENTION

It is an object of the present invention to provide a biosensor for real time monitoring a selected aspect of an air conditioning or a refrigeration process and system.

In one disclosed embodiment, a biosensor is provided for detecting bacteria, fungi, metabolites, volatile organic compounds or specific allergens in a residential or commercial building air conditioning system.

In another disclosed embodiment, a biosensor is provided for detecting the presence of refrigerant leaking from the evaporator coils in a residential or commercial system. The detection of refrigerant leaks is of critical concern because of potential adverse atmospheric environmental effects and the toxicity characteristics of several alternative refrigerants.

In a further disclosed embodiment, a biosensor is provided for detecting the growth of bacteria or fungi in an air conditioning or a refrigeration system; such as, for example, detecting the presence of Legionella bacteria in a commercial building air conditioning system, water heater or cooling tower, or detecting the presence of *Ecoli* bacteria in a refrigerated food storage container.

In a still further disclosed embodiment, a biosensor is provided for detecting the presence and/or measuring the concentration of certain metabolites indicative of fruit or vegetable ripening or food spoilage, for example ethylene, in a refrigerated food storage container.

In a still further disclosed embodiment, a biosensor is provided for detecting the presence and/or measuring the concentration of carbon dioxide in a refrigerated transport container for perishable products being maintained in a reduced oxygen environment. Such a biosensor may also be used to monitor the concentration of carbon dioxide in a room so as to provide a control signal for use in controlling ventilation of fresh air into the room.

In a still further disclosed embodiment, a biosensor is provided for detecting the presence of a chemical that is a byproduct of corrosion of a metal component.

In a still further disclosed embodiment, a biosensor is provided for detecting the presence of hydrogen gas in absorption chiller, such as, for example, an absorption chiller of a commercial building air conditioning system. The hydrogen gas concentration within the chiller is indicative of the amount of corrosion within the chiller.

BRIEF DESCRIPTION OF THE DRAWING

A more complete understanding of the present invention is presented in the following detailed description of various embodiments thereof wherein reference is made to the accompanying drawing wherein.

DESCRIPTION OF THE PREFERRED EMBODIMENTS

Figure 1:
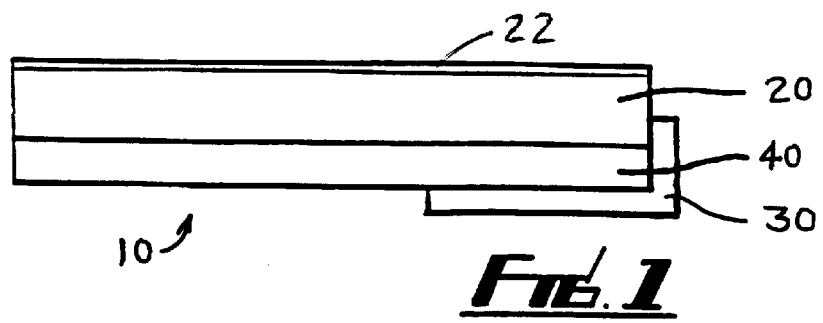
FIG. 1 is a sectional side elevation view of a biosensor in accordance with one aspect of the present invention.

Referring now to FIG. 1, there is depicted a biosensor 10 suitable for real time monitoring a selected aspect of a heating, ventilating, air conditioning or refrigeration process or other climate control process. The biosensor 10 includes a biocomponent element 20 carrying a bioagent 22 operative to detect one or more analytes indicative of the selected aspect of the climate control process to be monitored. As depicted in FIG. 1, the biocomponent element 20 is supported in cantilevered fashion on a base sensor element 30 that is also operative to generate a measurable output signal from an input signal. An interface layer 40 extends over at least a portion of the base sensor element 30 intermediate and in contact with both the biocomponent element 20 and the base sensor element 30. Although depicted in FIG. 1 as a micro-cantilever biosensor, it is to be understood that the biosensor 10 may be formed in other physical configurations without departing from the spirit and scope of the present invention.

Figure 2:
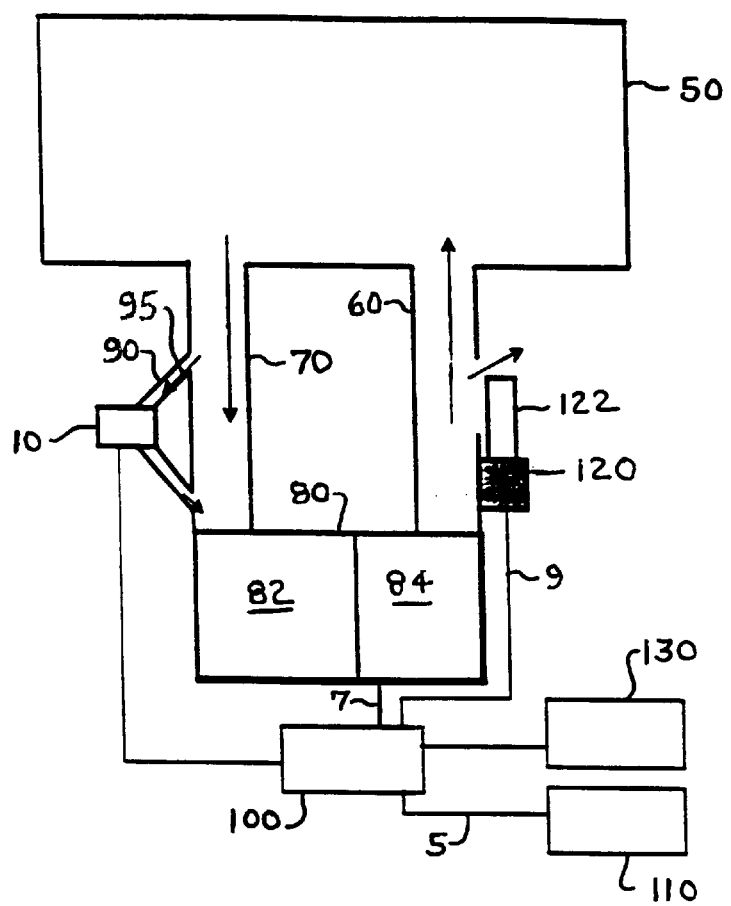
FIG. 2 is a diagrammatic representation of a climate control process monitored with a biosensor in accordance with the present invention.

Each analyte constitutes a particular volatile organic compound produced by a microorganism as a byproduct of its metabolic processes that is present in the gas or air associated with the climate control process. By using the biosensors of the present invention to monitor the climate control process for the presence of a specific analyte, the process may be controlled to reduce the level of the analyte or mitigate against the impact of the analyte. Referring now to FIG. 2, there is depicted therein a process for monitoring a climate control process in accordance with the present invention. Air or gas from the climate controlled environment within the enclosure 50 circulates, either continually or on demand, via the return duct 60 and the supply duct 70 through the process unit 80, which includes a climate control unit 82, for example, a heating unit, filtration unit, an air conditioning unit, a ventilating unit, a refrigeration unit or the like. Advantageously, the process unit 80 may also include a contamination removal device 84, such as a scrubber, an absorber, a reactor or the like, for extracting at least a portion of the undesired analyte from the air or gas stream passing through the process unit 80.

To monitor the air or gas from the climate controlled environment for the presence of one or more analytes, a relatively small portion 95 of the air or gas stream 75 diverts from the return duct 70 through bypass duct 90 and returns to the return duct 70 at a downstream point. The biosensor 10 is disposed in operative association with the bypass duct 90 to sense the presence of the analyte in the bypass stream 95. In operation, the biocomponent element 20 of the biosensor 10 interacts with the analyte and generates input signal to the base sensor element 30 of the biosensor 10. The base sensor element 30 generates an output signal 3 that is indicative of at least the presence of a preselected level of analyte or of the actual amount of analyte in the bypass stream 95.

A controller 100 receives and processes the output signal 3, for example a continuous voltage signal, from the sensor element 30 and responds appropriately, either to the absolute value of the signal or to the rate of change of the signal. For example, if the controller 100 determines that the concentration of analyte as indicated by the output signal 3 is undesirable, for example in excess of a preselected set point value, the controller 100 generates and outputs a control signal to initiate an appropriate system response. For example, the controller 100 may send a control signal 5 to activate an alarm 110. The controller may also send a control signal 7 to activate the contaminant removal device 84 or send a control signal 9 to the actuator 120 to open a vent door 122 associated with the supply duct 60 to vent a portion of the air or gas passing therethrough overboard.

In one embodiment of the present invention, a biosensor having a reactive biocomponent adapted for detecting the presence of a specific contaminant or related contaminants, such as mircoorganisms, for example fungi, or volatile organic compounds or particular allergens, is positioned in operative association with either the supply or return ducts of a HVAC system associated with a climate controlled personnel enclosure, such as for example a residential or commercial building, an automobile, a recreational vehicle, a bus, an aircraft, a train or ship cabin. The biocomponent element of the sensor generates an output indicative of the presence of the detected analyte and the sensor element generates a measurable signal which may be processed using a pattern recognition system whereby an estimate of the selected analyte, for example fungal count, the concentration of volatile organic compounds or allergen concentration, in the air stream passing to or from the enclosure. Some volatile organic compounds, generally known as microbial VOC or mVOC, have been identified as producing bad odor in buildings air conditioning systems, for example Geosmin, 1-octen-3-ol. Micro-cantilever sensors having each microcantilever coated with a specific adsorbent for the particular analyte to be detected and bioluminescent bioreporter sensors provided with genetically engineered specific bioreporters for detecting a particular analyte are particularly advantageous in this application. In this application, the biosensors 10 may, for example, comprises microcantilever sensors with bioagents using antigen-antibody binding interactions, bioluminescent sensors integrated directly on a microchip to detect light output, or biosensors with fiber optic probes integrated with immunoassay techniques.

Micro-cantilever based sensors may also advantageously be used for detecting leaking refrigerant in an air conditioning system. Several micro cantilever sensors, each being coated with a different plastic compound that adsorbs refrigerant, may be installed in an air conditioning duct in the vicinity of the evaporator coils. The plastic compounds are selected so that various refrigerants will have different solubilities in the respective selected plastics. Refrigerant solubility in a given plastic, to a large extent, depends upon refrigerant dipole moment and vapor pressure. The ratios of refrigerant solubilities in a suite of coated cantilevers will provide a unique pattern for each respective refrigerant. Refrigerant concentration can also be measured since the total weight of adsorbed refrigerant is related to its ambient pressure. A biosensor that reacts to an anaerobic environment could also be used to signal presence of refrigerant. Such a sensor may incorporate a methanogenic culture or active enzyme that produces an acid or other byproduct upon reaction with the refrigerant. Detection of the acid or other byproduct may be noted by a color change or the generation of light through fluorescent molecules.

Micro-cantilever based sensors may also be advantageous for detecting the presence of leaks in absorption chillers, such as water chillers commonly used in large commercial building air conditioning systems. Typically, if a leak exists, oxygen in the air leaking into the chiller will accelerate corrosion. Because hydrogen is produced as a result of corrosion within the absorption chiller, the production of hydrogen will accelerate and the biosensor will operate as a real-time corrosion detector. Using conventional techniques, corrosion in the interior of an operating absorption chiller is extremely difficult to monitor and requires extensive manual labor and operational disruption. In accordance with this aspect of the present invention, the presence of a leak and of corrosion within the chiller is detected in a non-intrusive fashion by a biosensor positioned externally to the chiller.

In other aspect of the invention, biosensors are provided for detecting the presence of bacteria. *Ecoli* bacteria are known to grow in food compartments if proper temperature is not maintained. Pathogenic Legionella bacteria may under certain conditions exist in cooling tower water and in some instances be entrained in the conditioned air in a building air conditioning system. A biosensor having a biocomponent element coated, impregnated or otherwise treated with *Ecoli* or Legionella specific antibodies, as the respective application dictates, could be used for online monitoring of *Ecoli* in food storage containers or display cases and Legionella in cooling tower water. Micro-cantilever biosensors having cantilever elements coated with the selected specific antibodies, fiber optic probe biosensors having the tip of the fiber optic probe coated with the selected specific antibodies, and porous silicon sensors having the porous silicon surface coated with the selected specific antibodies are particularly advantageous for use in this application. These sensors could also be integrated with on-chip electronic circuitry. For example, *E-coli* may be detected using a surface plasmon resonance (SPR) technique, through binding antibodies, antigens, or enzymes to the surface of a thin film. Binding of the *E-coli* changes the optical properties of the film and shifts the wavelength of the resonant light, thereby indicating the presence of bacteria. Also, the binding of either bacteria with a specific antibody may also be detected using an amperometric or fluorescence response. Commercially available antibodies specific to Legionella or *E-coli* bacteria may be coated onto a sensor element such as magnetic beads which would be used to capture the bacteria from the air. Using a sandwich assay mechanism, captured bacteria may then be stained using an appropriately tagged antibody.

Biosensors of the present invention are also suitable for monitoring fruit ripening and perishable product quality preservation in perishable product refrigeration applications, such as refrigerated storerooms, refrigerated transport containers, trucks and trailers, and refrigerated display cases. In this application, the biosensors of the present invention have a biocomponent element coated, impregnated or otherwise treated with a particular bioagent operative to detect certain chemical species or metabolites that may be used as an indicator of the quality or freshness of fruits, vegetables, meats, and other foods. These sensors may be placed in refrigerated food storage units, including but not limited to transport containers, trailers and trucks, as well as in supermarket display cases, refrigerators, and freezers. For example, biosensors may be provided for monitoring the level of ethylene present in a refrigerated food storage unit as an indication of the ripening fruit and thereby provide a means for active feedback for improved ventilation, ethylene removal, or temperature reduction. Apart from ethylene in food storage applications, biosensors may be provided for monitoring the level of carbon dioxide present in a food storage unit and may be used to provide active feedback for controlling the food storage conditions. Bioluminescent bioreporter sensors having genetically engineering bioreporter organisms for ethylene or carbon dioxide and micro-cantilever biosensors coated, impregnated or otherwise treated with an adsorbent for ethylene or carbon dioxide are particularly advantageous for use in these applications.

Referring again to FIG. 2, in the example of a refrigerated fruit transport container, the biosensor 10 is disposed in a bypass duct 90 having an inlet opening to the air intake duct 70 from the container 50 and an outlet opening back to the air intake duct 70 downstream of the inlet and upstream of the refrigeration unit 82. A small amount of air is bled off through the bypass duct 90 to the biosensor 10 which preferably has continuous monitoring capability and a response time of under 10 minutes. The biosensor 10 may advantageously include a biocomponent element 20 that changes its optical density when exposed to ethlyene, such as for example, palladium and molybdenum based complexes, operatively associated with a base sensor element 30, such as for example a phototransistor, that measures the intensity of the light passing through the biocomponent element 20 and generates a voltage signal that is indicative of the measured light intensity. In operation, a light beam of a preselected intensity from a light source (not shown) is directed upon the biocomponent element 20 and the light intensity passing through the biocomponent element 20 measured by the sensor element 30. The controller 100 receives the voltage signal from the sensor element 30, compares that signal to a set point voltage indicative of 100% light transmission through the biocomponent element 20, and determines the ethylene concentration present in the air from the container 50 from the difference between the set point voltage and the received voltage signal.

The controller 100 compares the measured ethylene concentration to an operated specified set point concentration representative of the acceptable level of ethylene. If the measured concentration exceeds the set point concentration, the controller 100 generates and transmits a control signal to the vent actuator to open the vent door. A portion of the air returning to the container 20 through the return duct 60 will pass overboard through the opening provided by the open vent door to be replaced by make-up air from the refrigeration unit 82. As the sensor 10 continuously monitors the ethylene concentration, the controller 100 will recognize when the ethylene concentration has returned to an acceptable level and thereupon send a signal to the vent actuator to close the vent door. The controller 100 may also be equipped to monitor the functionality of the biosensor 10 and generate and transmit an alarm signal in the event that the biosensor 10 has malfunctioned or been in operation beyond a specified number of hours. Some biosensors may require periodic recharging or replacement of the bioagent, for example as a function of time or of the voltage level output of the biosensor. Accordingly, the controller 100 may incorporate a timer to record how long the biosensor has been operating, or a detector to sense changes in functionality indicating the need for replacement or recharging, and trigger an alarm to alert the user.

Further, the controller 100 may be connected to additional sensors, either biosensors or conventional sensors, to monitor temperature, humidity, carbon dioxide, oxygen and nitrogen levels in the circulating air and pass that information to a data reorder 130. The output of the biosensor 10 and of the controller 100 may also be recorded by the date recorder 130 to provide a record of the time-concentration history of how much ethylene was present in the container during a transport/storage operation. More specifically, a "smart card" or "receipt" may be employed that would record the concentration of ethylene, as well as temperature, humidity, carbon dioxide, oxygen and nitrogen, as desired.

Biosensors may also be provided for sensing chemical species generated during the corrosion process of metals as a means of detecting incipient corrosion of metal components. For example, microbial induced corrosion of structural components is a growing concern in heating, ventilating and air conditioning systems. Species produced as a result of microbial induced corrosion include, for example, organic acids. Additionally, the presence of formic acid may be indicative of formicary corrosion. By detecting the presence of these species, the health of structural or specific components may be continuously or periodically and remotely monitored. Micro-cantilever based sensors coated, impregnated or otherwise treated with specific adsorbents for the organic salts or formic acid produced during the corrosion process are particularly advantageous for this application. Bioluminescent bioreporter sensors and porous silicon biosensors are also useful in this application.

What is claimed is:

1. An apparatus for detecting a leak of refrigerant from an evaporator coil of an air conditioning apparatus, the evaporator coil disposed in a air flow duct associated with the air conditioning apparatus, comprising:

a biosensor disposed in the air conditioning duct in the vicinity of the evaporator coil, said biosensor having a biocomponent element including a bioagent operative to detect refrigerant leaking from the evaporator coil; and a sensor element operatively associated with the biocomponent element for generating a measurable output signal indicative of the presence of the refrigerant.

2. An apparatus for detecting the occurrence of corrosion within the interior of an absorption apparatus utilizing a process gas to chill a fluid, comprising:

a biosensor disposed in contact with the process gas at a location external of the absorption chiller, said biosensor having a biocomponent element including a bioagent operative to detect hydrogen gas in the process gas from the absorption chiller.

3. An apparatus for detecting the occurrence of corrosion within a heating, ventilating or air conditioning system having an air flow duct, comprising:

a biosensor disposed in the air conditioning duct, said biosensor having a biocomponent element including a bioagent operative to detect a chemical byproduct of corrosion of a metal component; and a sensor element operatively associated with the biocomponent element for generating a measurable output signal indicative of the presence of the chemical byproduct.

4. An apparatus as recited in claim 5 wherein said biosensor is coated with a plastic compound the adsorbs refrigerant.

* * * * *